United States Patent [19]
Aiyar et al.

[11] Patent Number: 6,074,845
[45] Date of Patent: Jun. 13, 2000

[54] NUCLEIC ACID ENCODING A BOVINE CALCITONIN RECEPTOR-LIKE RECEPTOR (BECRLR)

[75] Inventors: Nambi V. Aiyar, Berwyn; Jyoti Disa, King of Prussia, both of Pa.

[73] Assignee: SmithKline Beecham Corporation, Philadelphia, Pa.

[21] Appl. No.: 09/238,796

[22] Filed: Jan. 28, 1999

[51] Int. Cl.[7] .............................. C12N 15/12; C12N 5/10; C12N 15/63; C07K 14/705
[52] U.S. Cl. ................. 435/69.1; 435/71.1; 435/71.2; 435/252.3; 435/254.11; 435/320.1; 435/325; 435/471; 536/23.1; 536/23.5; 536/24.3; 536/24.31; 536/24.5; 530/350
[58] Field of Search ........................ 530/350; 536/23.1, 536/23.5, 24.3, 24.31; 435/69.1, 71.1, 71.2, 325, 371, 252.3, 254.11, 320.1, 24.5

[56] References Cited

PUBLICATIONS

Cunningham et al. (1989) Science, vol. 24,4 pp. 1081–1085.
George et al. (1988) Macromolecular Sequencing & Synthesis Selected Methods and Applications, pp. 127–149, ch, 12, Alan R. Liss, Inc.
Fluhmann et al. (1995) Biochemical & Biophysical Research Communcations, vol. 206, No. 1, pp. 341–367.
Aiyar, et al. "A cDNA Encoding the Calcitonin Gene–related Peptide Type 1 Receptor", The Journal of Biological Chemistry, vol. 271 (19) pp. 11325–11329 (1996).
GenBank Accession No. L76380. Aiyar et al. Aug. 13, 1996.

*Primary Examiner*—Prema Mertz
*Attorney, Agent, or Firm*—Elizabeth J. Hecht; Ratner & Prestia; William T. King

[57] ABSTRACT

BECRLR polypeptides and polynucleotides and methods for producing such polypeptides by recombinant techniques are disclosed. Also disclosed are methods for utilizing BECRLR polypeptides and polynucleotides in screening assays to discover compounds that either agonize or antagonize the biological activity of the receptor. Such compounds are expected to be useful in treatment of human diseases, including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome.

15 Claims, No Drawings

NUCLEIC ACID ENCODING A BOVINE CALCITONIN RECEPTOR-LIKE RECEPTOR (BECRLR)

FIELD OF THE INVENTION

This invention relates to newly identified polypeptides and polynucleotides encoding such polypeptides, to their use in therapy and in identifying compounds that may be agonists or antagonists that are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterize further genes and their related polypeptides/proteins, as targets for drug discovery.

It is well established that many medically significant biological processes are mediated by proteins participating in signal transduction pathways that involve G-proteins and/or second messengers, e.g., cAMP (Lefkowitz, Nature, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., Proc. Natl Acad. Sci., USA, 1987, 84:46–50; Kobilka, B. K., et al., Science, 1987, 238:650–656; Bunzow, J. R., et al., Nature, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., Science, 1991, 252:802–8).

For example, in one form of signal transduction, the effect of hormone binding is activation of the enzyme, adenylate cyclase, inside the cell. Enzyme activation by hormones is dependent on the presence of the nucleotide, GTP. GTP also influences hormone binding. A G-protein connects the hormone receptor to adenylate cyclase. G-protein was shown to exchange GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (otherwise known as 7TM receptors) have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include, but are not limited to, calcitonin, adrenergic, endothelin, cAMP, adenosine, muscarinic, acetylcholine, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise hydrophilic sockets formed by several G-protein coupled receptor transmembrane domains, said sockets being surrounded by hydrophobic residues of the G-protein coupled receptors. The hydrophilic side of each G-protein coupled receptor transmembrane helix is postulated to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., Endoc. Rev., 1989, 10:317–331). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host. Over the past 15 years, nearly 350 therapeutic agents targeting 7 transmembrane (7 TM) receptors have been successfully introduced onto the market.

Polypeptides of the present invention are believed to be members of the Calcitonin/ VIP/Secretin family of 7TM receptors family of polypeptides. They are therefore of interest because calcitonin gene-related peptide (CGRP) receptor belongs to this family of receptors. Calcitonin gene-related peptide (CGRP), amylin and adrenomedullin (ADM) belong to a family of structurally and biologically related polypeptides (Poyner, Trends Pharmacol. Sci., 1995, 16: 424–428.)

Calcitonin Gene-Related Peptide is a 37 amino acid polypeptide that is localized at nerve terminals present in the central and peripheral nervous systems (Goodman, Life Sci. 1986,38: 2169–2172) and is an extremely potent vasoactive substance which displays marked chronotropic, inotropic and vasodilatory effects in humans, and animals. (Fischer et al, *Bone Miner*, 1987,2, 347–359). Amylin is also a 37 amino acid peptide with 47% sequence identity with CGRP and plays a physiological role in regulating glucose metabolism in muscles (Rink et al, *Trends Pharmacol. Sci.*, 1993, 14: 113–118.). Human adrenomedullin (ADM), a 52 amino acid peptide, is a recently discovered vasodilating peptide implicated in the regulation of circulatory homeostasis and pathophysiology of cardiovascular diseases (Samson, *Frontiers in Neuroendocrinology* 1998,19: 100–127). These bioactive peptides share both the ring structure with a disulfide bridge and the C-terminal amide structure.

Adrenomedullin (ADM) is widely distributed in human tissues, including the adrenal medulla, kidney, and lung, and is found in human plasma, suggesting it may function as a circulating hormone. Studies have demonstrated that ADM is produced and secreted from cultured vascular smooth muscle cells (SMC) and vascular endothelial cells (Schell et al, *Trends Endocrinol Melab* 1996,7:7–13). When injected intravenously into rats, ADM elicited a strong, long-lasting hypotension, as a result of vasodilation in resistance arteries (Kangawa et al, *J. Cardiac Failure* 1996,2:S135–S140). Apart from the vasorelaxant effect, ADM has been implicated in the regulation of renal function by its potent natriuretic and diuretic properties, exhibits bronchodilatory effect and inhibits the release of aldosterone and ACTH. ADM has also been shown to down-regulate insulin secretion and blood glucose metabolism (Martinez et al, *Endocrinology* 1996, 137: 2626–2632). ADM effects are mediated through specific receptors via multiple intracellular transduction pathways (Shimekake et al, *J. Biol. Chem.* 1995, 270: 4412–4417). Using [$^{125}$I] rat ADM, specific binding sites were demonstrated on various rat tissues. Among the tissues tested, lung had the highest density of ADM binding sites. Studies have shown that ADM stimulates the accumulation of intracellular cAMP in vascular SMC, and bovine EC and induces a rise in intracellular $Ca^{++}$ through the activation of phospholipase C (Shimekake et al, *J. Biol. Chem.* 1995, 270: 4412–4417). ADM induces rapid and transient c-fos gene expression and AP-I DNA binding activity in rat vascular SMC and cardiomyocytes (Sato et al, *Biochem. Biophys. Res. Commun.* 1995, 217: 211–216). Further, ADM activated the NO-cGMP system in kidney, vascular EC and also in rabbit ventricular myocytes (Ikenouchi et al, *Circulation* 1997, 95:2318–2324). In normal humans, immunoreactive ADM has been reported to be present in plasma and urine (Kitamura et al, *FEBS Lett.* 1994, 341:288–290). In pathological states, the plasma concentration of ADM has been reported to be increased such as in class IV congestive heart failure (5-fold), acute myocardial infarction (5 fold) and the combination of both resulted in increased ADM levels by 10 fold (Massart et al, *Acta Cardiol.* 196, 51, 259–269). Evidence for cardiac secretion of ADM was also shown to be related to the severity of CHF in patients (Massart et al, *Acta Cardiol.* 196, 51, 259–269). In addition, the ADM level increased in chronic renal failure (4-fold), hypertension (2-fold), acute asthma attack (5 fold) and sepsis (13-fold). Studies have shown the up-regulation of ADM mRNA in a model of ischemic stroke (Jougasaki et al, *J. Clin. Invest.* 1996, 97, 2370–2376).

Calcitonin gene-related peptide is an extremely potent vasoactive substance which displays marked chronotropic, inotropic and vasodilatory effects in humans, and animals (Wimalawansa, *Endocrine Reviews* 1997,17:533–585). The vasodilator effect of CGRP is endothelium dependent or independent, depending on the vascular bed and species involved (Greenberg et al, *Br. J. Pharmacol* 1987,92, 789, Gray et al, *Eur. J Pharmacol* 1992, 212:37–42). Infusion of CGRP into humans, and a variety of other species produces vasodilation, increased regional blood flow, hypotension and tachycardia. Studies in rabbit mesenteric resistance arteries and rat basilar artery suggest that CGRP acts through an ATP-sensitive potassium channel to induce vasodilation since in these blood vessels CGRP actions are inhibited by glibenclamide (Nelson et al, *Nature* 1990, 344: 770–773). In addition to its vasodilatory effects, CGRP enhances the increase in vascular permeability induced by various inflammatory mediators including interleukin, PAF, histamine and bradykinin (McGillis et al, *Methods in Neuroscience, 1995, 24: 355–389*). CGRP also affects the glomerular filtration rate, renal blood flow, and secretion of renin and has been implicated in pain transmission at sensory spinal pathways in the dorsal horn of the spinal cord. Recent evidence also suggests that CGRP might inhibit the proliferation of smooth muscle cells (Fiscus, *FASEB J.*, 1993, 7, A791. Abstract 4567 ) and lipid peroxidation (Li et al, *Med Sci Res.*, 1995, 23:253–254). CGRP is a potent, indirect antagonist of insulin's effects on glucose metabolism. In "glucose clamp" studies in rats, CGRP was shown to produce "insulin resistance" exemplified by a rapid and sustained reduction in the glucose infusion rate needed to maintain plasma euglycemia during a constant insulin infusion rate (Molina et al, *Diabetes* 1990, 39: 260–265). Furthermore, CGRP was effective in blocking insulin inhibition of hepatic glucose production. Activation of sensory nerves by capsaicin and resiniferatoxin inhibits insulin-stimulated glycogen synthesis which correlates with an increase of CGRP released from sensory nerves in skeletal muscle. Thus, CGRP has been implicated as a mediator of cerebral vasodilation leading to migraine and may play a role in the onset of Type 11 diabetes (NIDDM) via promotion of insulin resistance.

Calcitonin gene-related peptide initiates its responses through an interaction with specific membrane receptors on target tissue that are primarily coupled to the activation of adenylyl cyclase. CGRP-mediated-activation of adenylyl cyclase have been identified and characterized in several tissues, including cardiac, endothelial and vascular smooth muscle (Poyner, *Pharmacol Ther* 1992, 56:23–51, Wimalawansa, *Endocrine Reviews*, 1997, 17:533–585.). The receptor for CGRP has been cloned from various species including human, rat and pig (Aiyar et al, *J Biol Chem* 1996, 271:11325–11329; Elshourbagy et al, *Endocrinology* 1998, 139:1678–1683; Han et al, *Mol Endocrinology.* 1997, 18:267–272; Njuki et al, *Clinical Sci* 1993. 85:385–388). These receptors show 91–95% identity at the amino acid level among species. Related calcitonin receptor like-receptors (CRLR) (Njuki et al, *Clinical Sci* 1993, 85: 385–388; Fluhmann et al, *Biochem Biophys Res Commun* 1995, 206:341–347) were reported previously but they were unable to identify the ligand. It is important to note that the expression of functional CGRP receptors could be accomplished only in human embryonic kidney 293 (HEK-293) cells. The CGRP receptor displays 7 transmembrane domains and shows significant homology with a subfamily of G-protein coupled receptors that includes calcitonin, vasoactive intestinal peptide, secretin, glucagon and corticotropin releasing factor (Segre et al, *Trends Endocrinol Metab* 1993, 4:309–314). Messenger RNA encoding the CGRP receptor is expressed in relatively high levels in human heart and lung. Expression of the recombinant CGRP receptor in stably transfected HEK 293 cells has enabled study of their ligand stimulated signal transduction. Like other receptors of this family, the recombinant CGRP receptor was shown to be capable of activating adenylyl cyclase as well as rapidly increasing intracellular calcium through the activation of phospholipase C (Aiyaret al, *Mol Cellular Biochem* 1998 (in press)).

Recent evidence (McLatchie et al, Nature 1998, 393, 333–339) suggests that the related peptides, CGRP and ADM, bind to the same seven transmembrane receptor, with receptor specificity being determined by a receptor associated modifying proteins (RAMPs). They demonstrated that when the calcitonin receptor like receptor (CRLR) is coexpressed with RAMP 1, the expressed receptor responds to CGRP. On the other hand, when CRLR is co-expressed with RAMP2, the expressed receptor responds to ADM. Thus, CRLR has been shown to act as both CGRP and ADM receptors which depend upon the cellular expression of specific RAMPs.

SUMMARY OF THE INVENTION

The present invention relates to bovine calcitonin receptor-like receptor (herein after referred to as "BECRLR"), in particular BECRLR polypeptides and BECRLR polynucleotides, recombinant materials and methods for their production. In another aspect, the invention relates to methods for using such polypeptides and polynucleotides, including the development of new drugs for the treatment of human diseases, including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome, hereinafter referred to as "the Diseases", amongst others In a further aspect, the invention relates to methods for identifying agonists and antagonists/inhibitors using the materials provided by the invention, and treating conditions associated with BECRLR imbalance with the identified compounds The present invention further relates to methods for creating transgenic animals and knock-out animals. Furthermore, this invention relates to transgenic and knock-out animals obtained by using these methods. Such animal models are expected to provide valuable insight into the potential pharmacological and toxicological effects in humans of compounds that are discovered by the aforementioned screening methods. An understanding of how the BECRLR gene functions in these animal models is expected to provide an insight into treating and preventing human diseases including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome, among others.

DESCRIPTION OF THE INVENTION

In a first aspect, the present invention relates to BECRLR polypeptides. Such peptides include isolated polypeptides comprising an amino acid sequence having at least a 95% identity, and most preferably at least a 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least a 95% identity, and most preferably at least a 97–99% identity, to the amino acid sequence of SEQ ID NO:2 over the entire length of SEQ ID NO:2. Such polypeptides include the polypeptide of SEQ ID NO:2.

The deduced amino acid sequence of the bovine CRLR was 92.4% and 87.9% identical to the human CGRP and the rat CT-like "orphan" receptor, respectively. This high degree of homology between the human and bovine amino acid sequences suggests that the plasmid encode the bovine CRLR is an ortholog of human CRLR.

These properties are hereinafter referred to as "BECRLR activity" or "BECRLR polypeptide activity" or "biological activity of BECRLR". Also included amongst these activities are antigenic and immunogenic activities of said BECRLR polypeptides, in particular the antigenic and immunogenic activities of the polypeptide of SEQ ID NO:2. Preferably, a polypeptide of the present invention exhibits at least one biological activity of BECRLR The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and lie; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to BECRLR polynucleotides. Such polynucleotides include isolated polynucleotides comprising a nucleotide sequence encoding a polypeptide having at least a 95% identity, to the amino acid sequence of SEQ ID NO:2, over the entire length of SEQ ID NO:2. In this regard, polypeptides having at least a 97% identity are highly preferred, while those with at least a 98–99% identity are more highly preferred, and those with at least a 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence having at least a 95% identity, to a nucleotide sequence encoding a polypeptide of SEQ ID NO:2, over the entire coding region. In this regard, polynucleotides having at least a 97% identity are highly preferred, while those with at least a 98–99% identity are more highly preferred, and those with at least a 99% identity are most highly preferred.

Further polynucleotides of the present invention include isolated polynucleotides comprising a nucleotide sequence having at a 95% identity, to SEQ ID NO:1 over the entire length of SEQ ID NO:1. In this regard, polynucleotides which have at least 97% identity are highly preferred, whilst those with at least 98–99% identify are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with Homo sapiens (Clone HSNME29) CGRP type-1 receptor, which has been published by Aiyar, N, et. al., Journal of Biological Chemistry. 271 (19), 11325–11329 (1996) and Njuki F, et al., Clin. Sci. 85 (4), 385–388 (1993).

The nucleotide sequence of SEQ ID NO:1 is a cDNA sequence and comprises a polypeptide encoding sequence (nucleotide 403 to 1791) encoding a polypeptide of 462 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of SEQ ID NO:2 is structurally related to other proteins of the VIP/Secretin family of 7TM receptors family, having homology and/or structural similarity with Homo sapiens (Clone HSNME29) CGRP type-1 receptor, which has been published by Aiyar. N., et. al., Journal of Biological Chemistry. 271 (19), 11325–11329 (1996) and Njuki. F., et. al., Clin. Sci. 85 (4), 385–388 (1993).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one BECRLR activity.

Polynucleotides of the present invention may be obtained, using standard cloning and screening techniques, from a cDNA library derived from mRNA in cells of bovine aortic endothelial cell cDNA library, using the expressed sequence tag (EST) analysis (Adams, M. D., et al. Science (1991) 252:1651–1656; Adams, M. D. et al., Nature, (1992) 355:632–634:, Adams, M. D., et al., Nature (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentzet al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides that are identical or have sufficient identity to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than bovine) that have a high sequence similarity to SEQ ID NO:1, typically at least 95% identical. The probes or primers will generally comprise at least 15 nucleotides, preferably, at least ;0 nucleotides and may have at least 50 nucleotides. Particularly preferred probes will have between 30 and 50 nucleotides, and may even have at least 100 nucleotides.

A polynucleotide encoding a polypeptide of the present invention, including homologs and orthologs from species other than bovine, may be obtained by a process which comprises the steps of screening an appropriate library under stringent hybridization conditions with a labeled probe having the sequence of SEQ ID NO:1 and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1× SSC at about 65° C. Thus the present invention also includes polynucleotides, preferably of at least 100 nucleotides in length, obtained by screening an appropriate library under stringent hybridization conditions with a labeled probe having the sequence of SEQ ID NO:1.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerization reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998– 9002, 1988). Recent modifications of the technique, exemplified by the Marathon™' technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells that are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrooket al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

The BECRLR gene products can be expressed in transgenic animals. Animals of any species, including, but not limited to: mice, rats, rabbits, guinea pigs, pigs, micro-pigs, goats, and non-human primates, e.g., baboons, monkeys, chimpanzees, may be used to generate BECRLR transgenic animals.

This invention further relates to a method of producing transgenic animals, preferably cows, over-expressing BECRLR, which method comprises the introduction of several copies of a segment comprising at least the polynucleotide sequence encoding SEQ ID NO:2 with a suitable promoter into the cells of a cow embryo at an early stage.

This invention also relates to transgenic animals, characterized in that they are obtained by he method of making transgenic cows, as defined above.

Any technique known in the art may be used to introduce the BECRLR transgene into animals to produce the founder line of animals. Such techniques include, but are not limited to: pronuclear microinjection (U.S. Pat. No. 4,873,191); retrovirus mediated gene transfer into germ lines (Van der Putten, et al., *Proc. Natl. Acad. Sci., USA* 82: 6148–6152 (1985); gene targeting in embryonic stem cells (Thompson, et al., *Cell* 56: 313–321 (1989); electroporation of embryos (Lo, *Mol. Cell Biol.* 3: 1803–1814 (1983); and spermmediated gene transfer (Lavitrano, et al., *Cell* 57: 717–723 (1989); etc. For a review of such techniques, see Gordon, *Intl. Rev. Cytol.* 115: 171–229 (1989).

A further aspect of the present invention involves gene targeting by homologous recombination in embryonic stem cells to produce a transgenic animal with a mutation in the BECRLR gene ("knock-out" mutation). In such so-called "knock-out" animals, there is inactivation of the BECRLR gene or altered gene expression, such that the animals can be useful to study the function of the BECRLR gene, thus providing animals models of human disease, which are otherwise not readily available through spontaneous, chemical or irradiation mutagenesis.

This invention further relates to a method of producing "knock-out" animals, preferably mice, no longer expressing the murine ortholog of BECRLR. By using standard cloning techniques, the BECRLR cDNA (SEQ ID NO:1) can be used as a probe to screen suitable libraries to obtain the genomic DNA clone of the murine ortholog of BECRLR. Using the murine genomic clone, the method used to create a knockout mouse is characterized in that:

- a suitable mutation is produced in the polynucleotide sequence of the murine ortholog genomic clone, which inhibits the expression of the gene that encodes the receptor, or inhibits the activity of the gene product;
- the said modified murine BECRLR polynucleotide is introduced into the homologous segment of murine genomic DNA, combined with an appropriate marker, so as to obtain a labeled sequence containing the modified murine genomic DNA;
- the said genomic DNA comprising the modified polynucleotide is transfected into embryonic stem cells and correctly targeted events selected in vitro; then
- the said stem cells are reinjected into a mouse embryo; then
- the said embryo is implanted into a female recipient and brought to term as a chimera which transmits the said mutation through the germline; and
- homozygous recombinant mice are obtained at the F2 generation which are recognizable by the presence of the marker.

Various methods for producing mutations in non-human, mammalian animals are contemplated and well known in the art. In a preferred method, a mutation is generated in a murine BECRLR allele by the introduction of a DNA construct containing DNA of a gene encoding murine BECRLR, which murine gene contains the mutation. The mutation is targeted to the allele by way of the DNA construct. The DNA of the gene encoding murine calcitonin receptor-like receptor contained by the construct may be foreign to the species of which the recipient is a member, may be native to the species and foreign only to the individual recipient, may be a construct comprised of synthetic or natural genetic components, or a mixture of these. The mutation may constitute an insertion, deletion, substitution, or combination thereof. The DNA construct can be introduced by, for example, calcium-phosphate DNA co-precipitation. It is preferred that a mutation be introduced into cells using electroporation, microinjection, virus infection, ligand-DNA. conjugation, virus-ligand-DNA conjugation, and liposomes.

Another embodiment of the instant invention is "knock-out" animals, preferably mice, obtained by the method of producing recombinant mice as defined above, among others.

The transgenic and "knock-out" animals as defined above are a particularly advantageous model, from a physiological point of view, for studying 7 transmembrane receptors. Such animals will be valuable tools to study the function of the BECRLR gene. Moreover, such animal models are expected to provide information about potential toxicological effects in humans of any compounds that are discovered by the aforementioned screening methods. An understanding of how the calcitonin receptor-like receptor gene functions in these animal models is expected to provide an insight into treating and preventing human diseases including, but not limited to: infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergies; benign prostatic hypertrophy; migraine; vomiting; psychotic and neurological disorders, including anxiety, schizophrenia, manic depression, depression, delirium, dementia, and severe mental retardation; and dyskinesias, such as Huntington's disease or Gilles dela Tourett's syndrome.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Polypeptides of the present invention are responsible for many biological functions, including many disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists or antagonists so-identified may be natural or modified substrates, ligands, receptors, enzymes, etc., as the case may be, of the polypeptide; or may be structural or functional mimetics thereof (see Coligan et al., *Current Protocols in Immunology* 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring BECRLR activity in the mixture, and comparing the BECRLR activity of the mixture to a standard. Fusion proteins, such as those made from Fc portion and BECRLR polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

One screening technique includes the use of cells which express receptors of this invention (for example, transfected CHO cells) in a system which measures extracellular pH or intracellular calcium changes caused by receptor activation. In this technique, compounds may be contacted with cells expressing receptor polypeptides of the present invention. A second messenger response, e.g., signal transduction, pH changes, or changes in calcium level, is then measured to determine whether the potential compound activates or inhibits the receptor.

Another method involves screening for receptor inhibitors by determining inhibition or stimulation of receptor-mediated cAMP and/or adenylate cyclase accumulation. Such a method involves transfecting a eukaryotic cell with the receptor of this invention to express the receptor on the cell surface. The cell is then exposed to potential antagonists in the presence of the receptor of this invention. The amount of cAMP accumulation is then measured. If the potential antagonist binds the receptor, and thus inhibits receptor binding, the levels of receptor-mediated cAMP, or adenylate cyclase, activity will be reduced or increased. Another method for detecting agonists or antagonists for the receptor of the present invention is the yeast based technology as described in U.S. Pat. No. 5,482,835.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of potential polypeptide antagonists may include oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:
(a) a polypeptide of the present invention;
(b) a recombinant cell expressing a polypeptide of the present invention;
(c) a cell membrane expressing a polypeptide of the present invention; or
(d) antibody to a polypeptide of the present invention; which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:
(a) determining in the first instance the three-dimensional structure of the polypeptide;
(b) deducing the three-dimensional structure for the likely reactive or binding site(s) of an agonist, antagonist or inhibitor;
(c) synthesizing candidate compounds that are predicted to bind to or react with the deduced binding or reactive site; and
(d) testing whether the candidate compounds are indeed agonists, antagonists or inhibitors. It will be further appreciated that this will normally be an interactive process.

The following definitions are provided to facilitate understanding of certain terms used frequently hereinbefore.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Knock-out" refers to partial or complete suppression of the expression of a protein encoded by an endogenous DNA sequence in a cell. The "knock-out" can be affected by targeted deletion of the whole or part of a gene encoding a protein, in an embryonic stem cell. As a result, the deletion may prevent or reduce the expression of the protein in any cell in the whole animal in which it is normally expressed.

"Transgenic animal" refers to an animal to which exogenous DNA has been introduced while the animal is still in its embryonic stage. In most cases, the transgenic approach aims at specific modifications of the genome, e.g., by introducing whole transcriptional units into the genome, or by up- or down-regulating pre-existing cellular genes. The targeted character of certain of these procedures sets transgenic technologies apart from experimental methods in which random mutations are conferred to the germline, such as administration of chemical mutagens or treatment with ionizing solution.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNA.; containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, PROTEINS—STRUCTURE AND MOLECULAR PROPERTIES, 2nd Ed., T. E. Creighton, W. H. Freeman and Company, New York, 1993; Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994:, *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison WI. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y)$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein na is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLES

Example 1

Mammalian Cell Expression

The receptors of the present invention are expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G41 8-resistant clones analyzed.

Example 2

Ligand Bank for Binding and Functional Assays

A bank of over 200 putative receptor ligands has been assembled for screening. The bank comprises: transmitters, hormones and chemokines known to act via a human seven transmembrane (7TM) receptor; naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to initially screen the receptor for known ligands, using both functional (i.e. calcium, cAMP, microphysiometer, oocyte electrophysiology, etc, see below) as well as binding assays.

Example 3

Ligand Binding Assays

Ligand binding assays provide a direct method for ascertaining receptor pharmacology and are adaptable to a high throughput format. The purified ligand for a receptor is radiolabeled to high specific activity (50–2000 Ci/mmol) for binding studies. A determination is then made that the process of radiolabeling does not diminish the activity of the ligand towards, its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

Example 4

Functional Assay in Xenopus Oocytes

Capped RNA transcripts from linearized plasmid templates encoding the receptor cDNAs of the invention are synthesized in vitro with RNA polymerases in accordance with standard procedures. In vitro transcripts are suspended in water at a final concentration of 0.2 mg/ml.

Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in Ca2+ free Barth's medium at room temperature. The Xenopus system can be used to screen known ligands and tissue/cell extracts for activating ligands.

Example 5

Microphysiometric Assays

Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor of the present invention.

Example 6

Extract/Cell Supernatant Screening

A large number of mammalian receptors exist for which there remains, as yet, no cognate activating ligand (agonist). Thus, active ligands for these receptors may not be included within the ligands banks as identified to date. Accordingly, the 7TM receptor of the invention is also functionally screened (using calcium, cAMP, microphysiometer, oocyte electrophysiology, etc., functional screens) against tissue extracts to identify natural ligands. Extracts that produce positive functional responses can be sequentially subfractionated until an activating ligand is isolatedand identified.

Example 7

Calcium and cAMP Functional Assays

7TM receptors which are expressed in HEK 293 cells have been shown to be coupled functionally to activation of PLC and calcium mobilization and/or cAMP stimulation or inhibition.

Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Similarly, HEK 293 cells expressing recombinant receptors are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Example 8

Screening of Bovine Endothelial Cell cDNA Libraries

A bovine endothelial cell cDNA library was constructed using the k-Zap cDNA synthesis kit (Stratagene, La Jolla, Calif.) following the standard protocol. The human CGRP receptor c-DNA-coding sequence was used as a probe for the isolation of CRLR clones from an endothelial cell library. The probe was radiolabled with $[\alpha^{32}P]$ ATP by the random priming method and used to screen approximately $1\times10^6$ plaque-forming units of the endothelial CRLR cDNA library. Nylon filters (Hybond ) containing plaque lifts were hybridized at 42° in 5× SSC (SSC is 150 mM NaCl and 15 mM sodium citrate), 5× Denhardt's solution, 0.1% SDS and 20% formamide followed by autography. Hybridizing clones (8) were plaque purified, and the pBluescript-containing insert was rescued from the purifiedxphage by in vivo excision using the Exassist/Solar system (Stratagene) and was sequenced in both strands by the dideoxynucleotide chain termination reaction. Two oligonucleotide primers were designed to amplify the open reading frame of the novel bovine CRLR cDNA. PCR amplification was carried out. A recombinant of the novel bovine CRLR was produced by transfection in HEK-293 cells. Transfection was achieved by LipofectAMINE procedure (Life Technologies, Gaithersburg, Md.). Stable cell lines expressing this receptor were selected with G418 and screened for CGRP and ADM-dependent activation of adenylyl cyclase.

Example 9

Membrane Preparation

Cells from BECRLR-293 were scraped into ice-cold PBS and centrifuged for 10 min at 1000× g at 4° C. The pellet was resuspended in 10 mM Tris-HCl, pH 7.4, 10 mM Na-EDTA and homogenized using a Dounce ground glass homogenizer. The homogenate was centrifuged for 20 min at 12,000× g at 4° C. and the resultant membrane pellet was resuspended in 50 mM Tris-HCl, pH 7.4, 10 mM $MgCl_2$ and recentrifuged. The final pellet was resuspended in 50 mM Tris-HCl, pH 7.4, 10 mM $MgCl_2$ and assayed immediately.

Example 10

Determination of Adenylyl Cyclase Activity

Membrane-bound adenylyl cyclase activity was determined. Membranes [40–60 ug protein] were incubated in triplicate tubes in buffer containing 50 mM Tris-HCl, pH 7.4, 10 mM $MgCl_2$, 1.2 mM ATP, 1.0 $\mu$Ci $[\alpha^{32}P]ATP$, 0.1 mM cAMP, 2.8 mM phosphoenolpyruvate and 5.2 $\mu$g/ml myokinase in a final volume of 100 $\mu$l for 20 min at 30° C. The reactions were stopped with 1 ml of a solution containing 0.28 mM cAMP, 0.33 mM ATP and 22,000 dpm of $[^3H]cAMP$. $[^{32}P]cAMP$ was separated using sequential chromatography as the rate of conversion of $[(\alpha^{32}P]ATP$ to $[^{32}P]cAMP$ on Dowex and alumina columns (33). Adenylyl cyclase activities were determined in the absence (basal) or presence of various concentrations of rat ADM or h$\alpha$CGRP (1 pM to 1 $\mu$M). The effect of ADM (22–52), ADM (26–52) and h$\alpha$CGRP(8–37), on ADM-mediated activation of adenylyl cyclase was also determined.

Example 11

Radioligand binding

Saturation binding experiments were carried out using membranes prepared from BECRLR-293 cells pretreated in the absence or presence of ADM. The incubation mixture contained various concentrations of $[^{125}I]$ ADM (5 to 120 pM) and 40–60 $\mu$g of membrane protein in a final volume of 500 ul. Nonspecific binding was determined in the presence of 1 μM r ADM. After incubating for 30 min at 25° C., the reaction mixture was rapidly diluted with cold 0.9% NaCl and bound and free ligands were separated by filtration on glass fiber filters. In competition binding studies, the membranes were incubated with increasing concentrations of r ADM or CGRP (1 pM–1 uM) and 150 pM of [$^{125}$I] r ADM for 30 min. at 25° C.

Example 12

Cloning of a cDNA Encoding the BECRLR from Bovine Aortic Endothelial Cell Library The human CGRP-R cDNA, previously cloned in our laboratory (Aiyar et al, *J Biol Chem* 1996, 271:11325–11329) was used to probe the bovine aortic endothelial cell cDNA library. Several positive clones were identified. Nucleotide sequence analysis of a clone revealed that there is only one open reading frame, beginning at the methionine codon ATG (nucleotide, 403) and ending at a stop codon TGA (nucleotide 1789). The other 5 positive clones have an identical nucleotide sequence but differs in the length of the 5' untranslated region. Two potential in-frame ATG codons precede the open reading frame of the protein; however, as the second ATG most closely approximates a KOZAK consensus translation initiation site (Kozak, Proc Natl Acad Sci USA, 92: 2662–2666), it is probably the translation initiation codon. Consequently, the deduced polypeptide consists of 462 amino acid residues. with a calculated molecular mass of approximately 50.8 kDa (FIG. 1). This is similar to the size of the human CGRP receptor which is 461 amino acids with a calculated molecular mass of 50.7 kDa. The hydropathy profile of the CGRP receptor determined by the method of Kyte and Doolittle indicated the presence of seven hydrophobic regions (22–27 amino acid residues in length) which are likely to be membrane-spanning domains that form the seven-transmembrane motif found among G-protein-coupled receptors

Example 13 mRNA Size and Tissue Distribution

Tissue-specific expression of BECRLR encoding mRNA was investigated by Northern blot analysis of RNA from several human tissues. A major mRNA species of 5.4 kb was predominantly expressed in the lung, heart, skeletal muscle and ovary.

Example 14

Characterization of BECRLR

HEK293 cells transiently transfected with this clone responded to CGRP and ADM (100 M each) by stimulating adenylyl cyclase activity (60–80% over basal). This clone has been stably expressed in HEK293 cells using the LipofectAMINE procedure and analyzed for CGRP and ADM-mediated adenylyl cyclase activity. One of the positive clones (BECRLR #8) was fully characterized. Both CGRP and ADM -mediated the activation of adenylyl cyclase activity in a concentration-dependent manner (~300% over basal) with an EC50 values of 2.8 and 4.3 nM. There was no additive effect between CGRP and ADM, indicating that both ligands may be acting at the same receptor. Further, ADM-activated adenylyl cyclase activity was inhibited by increasing concentrations of ADM(22–52), ADM(26–52) (ADM receptor antagonists) and CGRP (8–37) with an IC50 values of 0.11,>10 and 2.2 uM respectively. The vector transfected HEK293 cell membranes did not respond to CGRP or ADM in activating adenylyl cyclase. To investigate further the functional results described in this study, a binding study using [$^{125}$I]rADM and [$^{125}$I]CGRP was performed to identify the presence of binding sites for both peptides in BE-CRLR (#8) cell membranes. [$^{125}$I] CGRP binding was very little and the affinity or number of binding sites was difficult to determine. On the other hand [$^{125}$I] rADM displayed specific binding in these membranes and was 80–90% of the total binding. Scatchard transformation of the specific binding from the saturation binding experiments revealed a single class of high affinity binding site with a dissociation constant (Kd) of 250 pM. The specificity of [$^{125}$I] rADM binding to BE-CRLR membranes was investigated by analyzing the displacement of this radioligand binding by ADM and related peptides. Human and rat ADM displaced [$^{125}$I] rADM binding with high affinity (IC50 values 2–4 nM). Human ADM(22–52) also displaced binding by approximately 15-fold less potent than ADM. Both CGRP and CGRP (8–37) were less potent in displacing [$^{125}$I] rADM binding.

Based on radioligand binding ([$^{125}$I] r ADM) and functional assays (activation of adenylyl cyclase) BECRLR is a novel receptor with higher affinity to ADM.

SEQUENCE INFORMATION

SEQ ID NO:1

```
  1 GAATTCGGCA CGAGGATCAC CAAGCTCTGC TAACTGGACC TCACTCTGCC

51 TCCAGGATCA TATTGCAAGG CTTTCACCCT TCCCCACCTT GCCTGGGGGT

101 ACATTTCCTC TGCGGAATCT CAGAAAATCA AATTCCATCC TAAGAATAGT

151 TCACCAAgAA TTTCCTTAGG AGCTGTTCTG GGTCATGACC TCCAGATTTA

201 AGACATTCTT CAAGACAATT TTGAATAGGA TCCAAgAGAA AATGTGATTT

251 GAGTCTGGAG ACAATTGTGA TTATCAGCTA ATCCTAAAAG CCCAGTGTAg

301 CTGACTGAAA AgAAAACATT ATTTGGAAgA TTGCTACAAT ATAAAGAAAA

351 GTTTCTTTTA GTTTGATTTA TATATATAGC ATATTTCATT TTGGCTTTAA

401 TGATGGAGAA AAAGTTTTTC CTGTCTTTTC TGTTCCTCTT GCCTTTTTTC

451 ATGATTCTtG TTaTAGCaGA ATCCGAAgAA gAgAACCCCg ATGACTTAAT
```

```
-continued
 501 TCAGCTGGGT GTTAcTAgAA ATAAAATCaT GACGGCTCaA TATGAATGTT
 551 ACCAAAAAAT TATGCAAGAC CCTGTTCAAC AAACAGAAGG CATTTACTGT
 601 AACAGAACcT GGGATGGGTG GCTGTGCTGG AAcGACGTCG CTGCGGGCAC
 651 GGAGTCAATG CAGCACTGCC GcGATTACTT TCAAGATTTT GATCCTTCAG
 701 AAAAAGTTAC AAAAATCTGT GACCAAGATG GAAACTGGTT TAGACATCCA
 751 GCAAGCAACA GAACATGGAC AAATTATACC CAATGTAATG TTAACACACA
 801 TGAGAAAGTG AAGACTGCAC TGAATTTGTT TtACCTGACT ATAATTGGAC
 851 ATGTATTATC TATTGCATCA CTGCTTATCT CACTTGGCAT ATTCTTTTAT
 901 TTCAAGAGCC TAAGTTGCCA AAGGATTACC TTGCACAAAA ATTTGTTCTT
 951 CTCTTTCGTT TGTAATTCTG TCATAACCAT CATTCATCTC ACTGCAGTGG
1001 CCAACAACCA GGCCTTAGTG GCCACAAATC CTGTTAGCTG TAAAGTGTCC
1051 CAGTTCATCC ATCTCTACCT GATGGGCTGT AActacTTTT GGATGCTTtG
1101 tGAAGGCATT tACCtACACA CGCTTGTTGT AGTGGCTGTA TTTGCAGAGA
1151 AGCAGCACTT GATGTGGTAT TATTTTCTTG GCTGGGGATT TCCATTGATT
1201 CCTGCTTGTA TTCACGCTGT TGCCAGAAGA TTATATTACA ATGACAACTG
1251 CTGGATCAGT TCTGATACGC AACTCCTCTA CATTATCCAT GGCCCAATTT
1301 GTGCTGCTTT ATTGGTGAAT CTTTTTTTCC TATTAAATAT TGTACGTGTT
1351 CTTATCACCA AGTTAAAAGT TACTCACCAA GCAGAATCCA ATCTGTACAT
1401 GAAAGCTGTG AGAGCTACGC TTATCCTGGT GCCGTTGCTT GGCATTGAAT
1451 TTGTGCTGAT TCCATGGCGA CCTGAAGGAA AGATTGCAGA AGAGATATAT
1501 GATTACATCA TAAACATCCT CATGCACTAT CAGGGTCTCT TGGTATCTAC
1551 AATTTtctGC TTCTTTAAtG GAGAGGTTCA AGCAATTcTG AGAAGAAACT
1601 GGAATCAATA TAAAATCCAA TTTGGAAACA ACTTTTCCCA CTCAGATACT
1651 CTCCGTAGTG CATCTTACAC GGTTTCAACA ATCAGCGATG GTACAGGTTA
1701 CAGTCACGAC TGTcTAAGTG AACACTTAAA TGGAAAAAGC ATCCACGATA
1751 CTGACAACGT GGTCATAAAA CCCGAAAAGT TATACGATTG ATAATAGAGG
1801 GTGTACTGCT GAACTAcTTT TTCCCACTCC TAACTCCAGG ATTTGGATCT
1851 CGTGCCGAAN TC SEQ ID NO:2
  1 MEKKFFLSFL FLLPFFMILV LAESEEENPD DLIQLGVTRN KIMTAQYECY
 51 QKIMQDPVQQ TEGIYCNRTW DGWLCWNDVA AGTESMQHCP DYFQDFDPSE
101 KVTKICDQDG NWFRHPASNR TWTNYTQCNV NTHEKVKTAL NLFYLTIIGH
151 VLSIASLLIS LGIFFYFKSL SCQRITLHKN LFFSFVCNSV ITIIHLTAVA
201 NNQALVATNP VSCKVSQFIH LYLMGCNYFW MLCEGIYLHT LVVVAVFAEK
251 QHLMWYYFLG WGFPLIPACI HAVARRLYYN DNCWISSDTQ LLYIIHGPIC
301 AALLVNLFFL LNIVRVLITK LKVTHQAESN LYMKAVRATL ILVPLLGIEF
351 VLIPWRPEGK IAEEIYDYII NILMHYQGLL VSTIFCFFNG EVQAILRRNW
401 NQYKIQFGNN FSHSDTLRSA SYTVSTISDG TGYSHDCLSE HLNGKSIHDT
451 DNVVIKPEKL YD*
```

What is claimed is:

1. An isolated polynucleotide comprising a polynucleotide sequence that has at least 95% identity to a nucleotide sequence which encodes a polypeptide comprising the amino acid sequence set forth in SEQ ID NO:2, wherein said polynucleotide sequence may include up to $n_n$ nucleotide alterations over the entire region coding for SEQ ID NO:2, wherein $n_n$ is the maximum number of nucleotide alterations and is calculated by the formula $$n_n \leq x_n - (x_n \cdot y),$$

in which $x_n$ is the total number of nucleotides which encode the amino acid sequence set forth in SEQ ID NO:2 and y has a value of 0.95, wherein any non-integer product of $x_n$ and y is rounded down to the nearest integer prior to subtracting such product from $x_n$.

2. The isolated polynucleotide of claim 1 which encodes a polypeptide comprising the amino acid sequence set forth in SEQ ID NO:2.

3. The isolated polynucleotide of claim 1 which encodes a polypeptide consisting of the amino acid sequence set forth in SEQ ID NO:2.

4. The isolated polynucleotide of claim 1 which is RNA.

5. The isolated polynucleotide of claim 1 which is DNA.

6. An expression system comprising a polynucleotide encoding a polypeptide comprising the amino acid sequence set forth in SEQ ID NO:2 when said expression system is present in a compatible host cell.

7. A process for producing a recombinant host cell comprising introducing into a cell the expression system of claim 6 such that the host cell, under appropriate culture conditions, produces said polypeptide.

8. A recombinant host cell produced by the process of claim 7.

9. A membrane of a recombinant host cell of claim 8 expressing said polypeptide.

10. A process for producing a polypeptide comprising culturing a host cell of claim 9 under conditions sufficient for the production of said polypeptide and recovering said polypeptide from the culture.

11. An isolated polynucleotide comprising a polynucleotide sequence that has at least 95% identity to the nucleotide sequence set forth in SEQ ID NO:1, wherein said polynucleotide sequence may include up to $n_n$ nucleotide alterations over the entire length of SEQ ID NO:1, wherein $n_n$ is the maximum number of nucleotide alterations and is calculated by the formula $$n_n \leq x_n - (x_n \cdot y),$$

in which $x_n$ is the total number of nucleotides set forth in SEQ ID NO:1 and y has a value of 0.95, wherein any non-integer product of $x_n$ and y is rounded down to the nearest integer prior to subtracting such product from $x_n$.

12. The isolated polynucleotide of claim 11 wherein said polynucleotide sequence comprises the nucleotide sequence set forth in SEQ ID NO:1.

13. An isolated polynucleotide that is fully complementary to an isolated polynucleotide comprising a nucleotide sequence encoding a polypeptide comprising the amino acid sequence set forth in SEQ ID NO:2.

14. The isolated polynucleotide of claim 13 that is fully complementary to the nucleotide sequence set forth in SEQ ID NO:1.

15. An isolated polynucleotide obtained by screening an appropriate library under stringent hybridization conditions with a probe comprising a nucleotide sequence which encodes a polypeptide comprising the amino acid sequence set forth in SEQ ID NO:2, said stringent hybridization conditions comprising incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA; followed by washing the filters in 0.1× SSC at about 65° C., wherein said polynucleotide comprises at least 50 nucleotide bases.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 1862 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
GAATTCGGCA CGAGGATCAC CAAGCTCTGC TAACTGGACC TCACTCTGCC TCCAGGATCA      60
TATTGCAAGG CTTTCACCCT TCCCCACCTT GCCTGGGGGT ACATTTCCTC TGCGGAATCT     120
CAGAAAATCA AATTCCATCC TAAGAATAGT TCACCAAGAA TTTCCTTAGG AGCTGTTCTG     180
GGTCATGACC TCCAGATTTA AGACATTCTT CAAGACAATT TTGAATAGGA TCCAAGAGAA     240
AATGTGATTT GAGTCTGGAG ACAATTGTGA TTATCAGCTA ATCCTAAAAG CCCAGTGTAG     300
CTGACTGAAA AGAAAACATT ATTTGGAAGA TTGCTACAAT ATAAAGAAAA GTTTCTTTTA     360
GTTTGATTTA TATATATAGC ATATTTCATT TTGGCTTTAA TGATGGAGAA AAAGTTTTTC     420
CTGTCTTTTC TGTTCCTCTT GCCTTTTTTC ATGATTCTTG TTATAGCAGA ATCCGAAGAA     480
GAGAACCCCG ATGACTTAAT TCAGCTGGGT GTTACTAGAA ATAAAATCAT GACGGCTCAA     540
TATGAATGTT ACCAAAAAAT TATGCAAGAC CCTGTTCAAC AAACAGAAGG CATTTACTGT     600
AACAGAACCT GGGATGGGTG GCTGTGCTGG AACGACGTCG CTGCGGGCAC GGAGTCAATG     660
CAGCACTGCC CCGATTACTT TCAAGATTTT GATCCTTCAG AAAAAGTTAC AAAAATCTGT     720
GACCAAGATG GAAACTGGTT TAGACATCCA GCAAGCAACA GAACATGGAC AAATTATACC     780
CAATGTAATG TTAACACACA TGAGAAAGTG AAGACTGCAC TGAATTTGTT TTACCTGACT     840
ATAATTGGAC ATGTATTATC TATTGCATCA CTGCTTATCT CACTTGGCAT ATTCTTTTAT     900
TTCAAGAGCC TAAGTTGCCA AAGGATTACC TTGCACAAAA ATTTGTTCTT CTCTTTCGTT     960
TGTAATTCTG TCATAACCAT CATTCATCTC ACTGCAGTGG CCAACAACCA GGCCTTAGTG    1020
GCCACAAATC CTGTTAGCTG TAAAGTGTCC CAGTTCATCC ATCTCTACCT GATGGGCTGT    1080
AACTACTTTT GGATGCTTTG TGAAGGCATT TACCTACACA CGCTTGTTGT AGTGGCTGTA    1140
TTTGCAGAGA AGCAGCACTT GATGTGGTAT TATTTTCTTG GCTGGGGATT TCCATTGATT    1200
CCTGCTTGTA TTCACGCTGT TGCCAGAAGA TTATATTACA ATGACAACTG CTGGATCAGT    1260
TCTGATACGC AACTCCTCTA CATTATCCAT GGCCCAATTT GTGCTGCTTT ATTGGTGAAT    1320
CTTTTTTTCC TATTAAATAT TGTACGTGTT CTTATCACCA AGTTAAAAGT TACTCACCAA    1380
GCAGAATCCA ATCTGTACAT GAAAGCTGTG AGAGCTACGC TTATCCTGGT GCCGTTGCTT    1440
GGCATTGAAT TTGTGCTGAT TCCATGGCGA CCTGAAGGAA AGATTGCAGA AGAGATATAT    1500
GATTACATCA TAAACATCCT CATGCACTAT CAGGGTCTCT TGGTATCTAC AATTTTCTGC    1560
TTCTTTAATG GAGAGGTTCA AGCAATTCTG AGAAGAAACT GGAATCAATA TAAAATCCAA    1620
TTTGGAAACA ACTTTTCCCA CTCAGATACT CTCCGTAGTG CATCTTACAC GGTTTCAACA    1680
ATCAGCGATG GTACAGGTTA CAGTCACGAC TGTCTAAGTG AACACTTAAA TGGAAAAAGC    1740
ATCCACGATA CTGACAACGT GGTCATAAAA CCCGAAAAGT TATACGATTG ATAATAGAGG    1800
```

```
GTGTACTGCT GAACTACTTT TTCCCACTCC TAACTCCAGG ATTTGGATCT CGTGCCGAAN      1860

TC                                                                    1862
```

(2) INFORMATION FOR SEQ ID NO:2:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Lys Lys Phe Phe Leu Ser Phe Leu Phe Leu Leu Pro Phe Phe
  1               5                  10                  15

Met Ile Leu Val Ile Ala Glu Ser Glu Glu Asn Pro Asp Asp Leu
             20                  25                  30

Ile Gln Leu Gly Val Thr Arg Asn Lys Ile Met Thr Ala Gln Tyr Glu
             35                  40                  45

Cys Tyr Gln Lys Ile Met Gln Asp Pro Val Gln Gln Thr Glu Gly Ile
 50                  55                  60

Tyr Cys Asn Arg Thr Trp Asp Gly Trp Leu Cys Trp Asn Asp Val Ala
 65                  70                  75                  80

Ala Gly Thr Glu Ser Met Gln His Cys Pro Asp Tyr Phe Gln Asp Phe
                 85                  90                  95

Asp Pro Ser Glu Lys Val Thr Lys Ile Cys Asp Gln Asp Gly Asn Trp
                100                 105                 110

Phe Arg His Pro Ala Ser Asn Arg Thr Trp Thr Asn Tyr Thr Gln Cys
             115                 120                 125

Asn Val Asn Thr His Glu Lys Val Lys Thr Ala Leu Asn Leu Phe Tyr
130                 135                 140

Leu Thr Ile Ile Gly His Val Leu Ser Ile Ala Ser Leu Leu Ile Ser
145                 150                 155                 160

Leu Gly Ile Phe Phe Tyr Phe Lys Ser Leu Ser Cys Gln Arg Ile Thr
                165                 170                 175

Leu His Lys Asn Leu Phe Phe Ser Phe Val Cys Asn Ser Val Ile Thr
             180                 185                 190

Ile Ile His Leu Thr Ala Val Ala Asn Asn Gln Ala Leu Val Ala Thr
             195                 200                 205

Asn Pro Val Ser Cys Lys Val Ser Gln Phe Ile His Leu Tyr Leu Met
210                 215                 220

Gly Cys Asn Tyr Phe Trp Met Leu Cys Glu Gly Ile Tyr Leu His Thr
225                 230                 235                 240

Leu Val Val Val Ala Val Phe Ala Glu Lys Gln His Leu Met Trp Tyr
                245                 250                 255

Tyr Phe Leu Gly Trp Gly Phe Pro Leu Ile Pro Ala Cys Ile His Ala
                260                 265                 270

Val Ala Arg Arg Leu Tyr Tyr Asn Asp Asn Cys Trp Ile Ser Ser Asp
             275                 280                 285

Thr Gln Leu Leu Tyr Ile Ile His Gly Pro Ile Cys Ala Ala Leu Leu
290                 295                 300

Val Asn Leu Phe Phe Leu Leu Asn Ile Val Arg Val Leu Ile Thr Lys
305                 310                 315                 320

Leu Lys Val Thr His Gln Ala Glu Ser Asn Leu Tyr Met Lys Ala Val
```

-continued

```
                        325                     330                     335
Arg Ala Thr Leu Ile Leu Val Pro Leu Leu Gly Ile Glu Phe Val Leu
            340                     345                 350

Ile Pro Trp Arg Pro Glu Gly Lys Ile Ala Glu Ile Tyr Asp Tyr
        355                     360                 365

Ile Ile Asn Ile Leu Met His Tyr Gln Gly Leu Leu Val Ser Thr Ile
        370                     375                 380

Phe Cys Phe Phe Asn Gly Glu Val Gln Ala Ile Leu Arg Arg Asn Trp
385                     390                     395                 400

Asn Gln Tyr Lys Ile Gln Phe Gly Asn Asn Phe Ser His Ser Asp Thr
                405                     410                 415

Leu Arg Ser Ala Ser Tyr Thr Val Ser Thr Ile Ser Asp Gly Thr Gly
                420                     425                 430

Tyr Ser His Asp Cys Leu Ser Glu His Leu Asn Gly Lys Ser Ile His
            435                     440                 445

Asp Thr Asp Asn Val Val Ile Lys Pro Glu Lys Leu Tyr Asp
    450                     455                     460
```